United States Patent
Li et al.

(10) Patent No.: US 7,777,079 B2
(45) Date of Patent: Aug. 17, 2010

(54) PREPARATION METHOD OF 2, 6-DICHLOR-4-TRIFLUOROMETHYL ANILINE

(75) Inventors: Huiyue Li, Zhejiang (CN); Jinghua Chen, Zhejiang (CN); Jiangwei Wu, Zhejiang (CN); Guirong Huang, Zhejiang (CN); Xinping Zhao, Zhejiang (CN); Kaiquan Wang, Zhejiang (CN)

(73) Assignee: Zhejiang Weihua Chemical Co., Ltd., Weishan Town, Dongyang, Zhejiang (CN)

( * ) Notice: Subject to any disclaimer, the term of this patent is extended or adjusted under 35 U.S.C. 154(b) by 0 days.

(21) Appl. No.: 12/408,899

(22) Filed: Mar. 23, 2009

(65) Prior Publication Data

US 2009/0240083 A1 Sep. 24, 2009

(30) Foreign Application Priority Data

Mar. 24, 2008 (CN) .................. 2008 1 0060862

(51) Int. Cl.
*C07C 209/10* (2006.01)
(52) U.S. Cl. .................. 564/407; 564/404; 564/405

(58) Field of Classification Search .................. None
See application file for complete search history.

(56) References Cited

U.S. PATENT DOCUMENTS 4,096,185 A * 6/1978 Seiwell .................. 564/407
4,388,472 A * 6/1983 Cartwright et al. ............ 560/21
6,479,703 B1 * 11/2002 Ancel et al. .................. 564/405

FOREIGN PATENT DOCUMENTS

EP 1528052 A1 * 5/2005

* cited by examiner

*Primary Examiner*—Brian J Davis
(74) *Attorney, Agent, or Firm*—Global IP Services; Tianhua Gu

(57) ABSTRACT

This invention is involved with a preparation method of 2,6-dichloro-4-trifluoromethyl-aniline. With this process, p-Chlorobenzotrifluoride is used as the starting material and subjected to halogenation reaction and ammoniation reaction and through separation of reaction products the desired 2,6-dichloro-4-trifluoromethyl-aniline is obtained. In addition, ammonia is recovered from the surplus ammonia water in ammoniation reaction. This applied invention in characterized by simple process, cheap and easy-available raw materials, high reaction yield and friendly environment.

10 Claims, No Drawings

PREPARATION METHOD OF 2, 6-DICHLOR-4-TRIFLUOROMETHYL ANILINE

CROSS REFERENCE TO THE RELATED PATENT APPLICATION

This application claims the priority of the Chinese patent application No. 200810060862.8 filed on Mar. 24, 2008, which application is incorporation herein by reference.

FIELD OF THE INVENTION

This invention belongs to field of organic chemistry technology, involves a preparation method of polyhalogen arylamine, and provides a new preparation method of 2,6-dichloro-4-trifluoromethyl-aniline.

BACKGROUND OF THE INVENTION 2,6-dichloro-4-trifluoromethyl-aniline is one of important pesticide intermediates and is used to prepare insecticidal pyrazole type compounds such as pyrazole type insecticide "Fipronil". There are several preparation methods of 2,6-dichloro-4-trifluoromethyl-aniline and generally with these processes, 3,4-Dichlorobenzotrifluoride as starting material is subjected to ammoniation and then subjected to halogenation. However, they usually result in high production cost, great volume of generated three-wastes and difficult treatment.

U.S. Pat. No. 4,096,185 and U.S. Pat. No. 4,388,472 describe a synthesis process by which p-Chlorobenzotrifluoride reacts with liquid ammonia reaction to form 4-trifluoromethyl-aniline and the latter is then subjected to ring chlorination to form 2,6-dichloro-4-trifluoromethyl-aniline. However, the reaction for prepare 4-trifluoromethyl-aniline shall be carried out under high-temperature and high-pressure and with mixture of cuprous chloride and potassium fluoride as catalyst and its conversion ratio and final yield are very low, which makes its application and popularization very difficult.

Recently, Europe patent EP1528052A1 describe a new process of synthesis of 2,6-dichloro-4-trifluoromethyl-aniline, with which p-Chlorobenzotrifluoride as start material is at first subjected to ring chlorination to form 3,4,5-Trichlorobenzotrifluoride and 3,4-Dichlorobenzotrifluoride and then the latter is subjected to fluoridization reaction and ammoniation reaction to form 2,6-dichloro-4-trifluoromethyl aniline. Since the chlorides are liable to dissolve in water, in this process the control of water is rather strict and thus the requirements on the equipment are rather high. In addition, in this process expensive solvent N-methylpyrrolidone is used during ammoniation reaction and it is difficult to recover. Hence this process is inapplicable to industrial production.

From the above description it is clear that the existing processes for preparation of 2,6-dichloro-4-trifluoromethyl aniline have the following weaknesses: 1. high production cost due to expensive raw materials, 2. complex process and difficult industrialization, 3. low reaction conversion ratio and yield ratio, great volume of generated three-wastes and difficult treatment.

DESCRIPTION OF THE INVENTION

This invention is to provide a preparation method of 2,6-dichloro-4-trifluoromethyl-aniline which is characterized by simple process, cheap and easy-available raw materials, high reaction yield, and friendly environment.

By this invention, the synthesis route of preparation of 2,6-dichloro-4-trifluoromethyl aniline includes 2 reactions (halogenation and ammoniation).

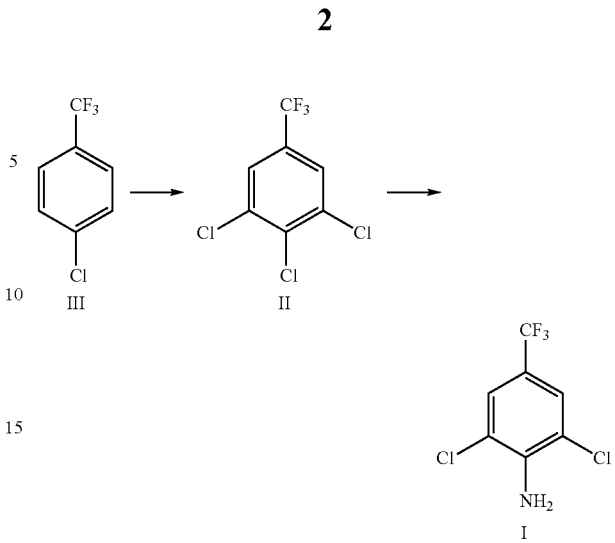

In the halogenation reaction, the elemental chlorine and p-Chlorobenzotrifluoride react under catalysis of composite catalyst consisting of elemental metal and metal halide and reaction temperature 50° C.~150° C. and this reaction needs no solvent. In composite catalyst, the elemental metal may be selected from common metals, e.g. iron and aluminum and the metal halide may be selected from common metal halides, e.g. ferric chloride and aluminum chloride. The composite catalyst preferentially consists of powdered iron and anhydrous ferric chloride. In the composite catalyst the dosage of the elemental metal is 0.2%~20% weight of the p-Chlorobenzotrifluoride, for an exemplary embodiment it is 0.2%~5%, the dosage of the metal halide is 0.2%~20% weight of the p-Chlorobenzotrifluoride, for an exemplary embodiment it is 1%~10%, and the mole ratio of elemental metal over the metal halide is 1:0.06~20.

The reaction is sampled, traced and analyzed with gas chromatography. When the peak of reaction the materials p-Chlorobenzotrifluoride disappears, the reaction is considered as completion and the feed ratio of the raw materials p-Chlorobenzotrifluoride over chlorine in halogenation reaction is calculated on basis of the chlorine volume supplied up to the completion. However, the feed mole ratio of the p-Chlorobenzotrifluoride over chlorine shall be 1:1~6.

After completion of reaction, crude product is obtained through routine separation method such as distillation and it is then rectified to obtain the high purity 3,4,5-Trichlorobenzotrifluoride.

In this invention, the main products of halogenation reaction include the 3,4-Dichlorobenzotrifluoride, the 3,4,5-Trichlorobenzotrifluoride and the 2,4,5-trichloro trifluoromethyl benzene, of which the 3,4,5-Trichlorobenzotrifluoride is the intermediate product and the 3,4-Dichlorobenzotrifluoride is the key intermediate for preparation of fluoro-bearing diphenyl ether type herbicide. Prior to this invention, usually this reaction had low selectivity. This invention is remarkably characterized that through optimization of the temperature, catalyst addition and feed ratio of halogenation reaction, it can effectively control yield of each reaction product, maximize yield of the 3,4,5-Trichlorobenzotrifluoride and keep isomer the 2,4,5-trichloro trifluoromethyl benzene and impurities within 11%.

This invention finds that, with other reaction conditions kept unchanged, increase of reaction temperature is advantageous to formation of target product. The adequate halogenation reaction temperature is 60° C.~120° C., for an exemplary embodiment it is 100° C.~120° C.

The ammoniation reaction utilizes intermediate product the 3,4,5-Trichlorobenzotrifluoride and ammonia water as raw materials and the proper reaction time is 1~30 h, for an exemplary embodiment it is 6~16 h and at the best it is 8~12 h. The raw material is ammonia water and the reaction needs no solvent.

On basis of 1 mol, the 3,4,5-Trichlorobenzotrifluoride, the dosage of ammonia (on base of liquid ammonia) is 6 mol~40 mol, adequately 10 mol~27 mol and preferentially 20 mol~26 mol. The reaction pressure is controlled within 1.0 MPa~13.5 MP, adequately 8.0 MPa~13.0 MPa and preferentially 11.0 MPa~12.0 MPa. The reaction temperature is controlled within 150° C.~178° C., adequately 155° C.~178° C. and preferentially 165° C.~175° C. Proper amount of water is added to make the mass percentage concentration of reaction-purpose concentration of the liquid ammonia is 60 wt %~80 wt %, and preferentially 65 wt %~78 wt %.

In this invention, the temperature of reactants is adjusted with steam or cooling water to indirectly control the reaction pressure at optimal value.

Through changing the mole ratio of the reaction materials and the mass percentage concentration of the concentration of the liquid ammonia, this invention eliminates the dependency on catalyst in the previous technologies and makes the ammoniation reaction possible under no catalyst and lower temperature, and increases yield of the target product.

This invention finds that, with other reaction conditions keep unchanged, with increase of feed of ammonia into the reaction material, the yield of 2,6-dichloro-4-trifluoromethyl aniline tends at first to increase and then decrease.

For example, when the mole ratio of the 3,4,5-Trichlorobenzotrifluoride cover ammonia (on liquid ammonia base) is 1:15, the yield of 2,6-dichloro-4-trifluoromethyl-aniline is 35%.

When the mole ratio of the 3,4,5-Trichlorobenzotrifluoride over ammonia (on liquid ammonia base) is 1:26, the yield of 2,6-dichloro-4-trifluoromethyl-aniline is 73%.

When the mole ratio of the 3,4,5-Trichlorobenzotrifluoride over ammonia (on liquid ammonia base) is 1:30, the yield of the 2,6-dichloro-4-trifluoromethyl-aniline is 65%.

In the above examples, the reaction conditions are: the reaction temperature 173° C., pressure 12.0 MPa, mass percentage concentration of ammonia water 73% and reaction time 11 h.

After completion of ammoniation reaction, ammonia is recovered for further utilization from the surplus the liquid ammonia through absorbing by 2-stage pressurized absorbing tanks. The pressure of the first stage absorbing tank is controlled at 0 MPa~2.5 MPa, and preferentially 0 MPa~2.0 MPa. In case of pressure in the first stage absorbing tank over 2.0 MPa, the second stage absorbing shall be conducted. The pressure of the second stage absorbing tank is controlled at 0 MPa~1.6 MPa and preferentially 0 MPa~1.2 MPa. After absorbing, mass percentage concentration of the liquid ammonia in the first and second stage absorbing tank is analyzed, the corresponding quantity of the liquid ammonia and to-be-supplemented liquid ammonia are calculated, and the recovery of ammonia is prepared to reaction-required high-concentration ammonia water for further ammoniation reaction.

In addition to recovery and utilization of surplus ammonia from reaction system, the crude reaction products are separated with routine rectification. For example, after washing high vacuum de-watering the crude product is rectified to obtain the 2,6-dichloro-4-trifluoromethyl-aniline of purity above 99%. Meanwhile, high purity unreacted the 3,4,5-Trichlorobenzotrifluoride is recovered for further ammoniation reaction.

The recovery of ammonia method used in this invention may completely or partially eliminate wasting of resource and environmental contamination. In this invention, surplus ammonia is recovered with water through absorbing by 2-stage pressurized absorbing tanks. During the ammonia absorption process, the concentration, temperature and partial pressure of ammonia in the liquid ammonia are 3 mutual related physical parameters. When any two of the 3 parameters are limited, the third parameter may be calculated on basis of rules of thermodynamics. In order to increase the absorbing efficiency of ammonia and keep the pressure of ammonia gas within the withstanding range of the absorbing tank, the temperature of the liquid ammonia shall be as low as possible. In this invention, during absorbing of ammonia, the absorbed solution is cooled with chilled saline so as to control the temperature, optimize ammonia gas pressure to close to its partial pressure and ensure high effective absorbing of ammonia gas. For example, if the ammonia gas is controlled at pressure not over 2.0 MPa, absorbed with normal temperature water, and during absorbing is cooled with chilled saline, the final temperature of absorbed solution is not above 35° C., and mass percentage concentration of ammonia water is not below 30%. In addition, in this invention stage-2 absorbing is adopted to ensure full recovery of ammonia and avoid environmental contamination.

The preparation method described here is friendly in environment, and high yield of target product. The used raw materials such as chlorine, ammonia (liquid ammonia), and p-Chlorobenzotrifluoride are cheap and easily available. The involved 2-step reaction needs no low-temperature treatment and the reactants immediately react after feed. The reaction temperature and pressure are not much strictly required. The reaction is moderate to avoid explosion and leakage of reactants. The products of 2-step reaction may be separated through simple distillation or rectification and the reaction process is very simple. The 3,4-Dichlorobenzotrifluoride formed in halogenation reaction is the key intermediate for preparation of fluoro-bearing diphenyl ether type herbicide, which enhances the feasibility if industrialization of this invention.

EXAMPLES

This invention is further described with following examples; however, this invention is not limited in these examples.

Example 1

Preparation of the 3,4,5-Trichlorobenzotrifluoride

Into a 1000 ml 4-neck flask add p-Chlorobenzotrifluoride 1000 g, metal powdered iron 6 g, and anhydrous aluminum chloride 10 g, start agitation, heat the mixed solution to 100° C., then slowly feed concentrated sulfuric acid-dried chlorine 1028 g under reaction temperature 110° C., take sample, make GC analysis and trace to judge the reaction end point, lower the temperature, discharge the products, and obtain mixed solution of chlorides. The mixed solution contains 82.46% the 3,4-Dichlorobenzotrifluoride, 5.25% the 3,4,5-Trichlorobenzotrifluoride and 12.29% 2,4,5-trichloro trifluoromethyl benzene and polychlorinated compounds.

Example 2

Preparation of the 3,4,5-Trichlorobenzotrifluoride II

Into a 1000 ml 3-neck flask add 99% p-Chlorobenzotrifluoride 1000 g, 6 g powdered iron and 12 g anhydrous ferric chloride, start agitation, heat the mixed solution to 85° C., then slowly feed concentrated sulfuric acid-dried chlorine 1124 g under controlled reaction temperature 105° C., make GC trace analysis till reaction end point, lower the temperature, discharge the products, and obtain mixed solution of chlorides containing 68.38% 3,4-Dichlorobenzotrifluoride, 21.42% the 3,4,5-Trichlorobenzotrifluoride and 10.20% 2,4,5-trichloro trifluoromethyl benzene and polychlorinated compounds. Rectify the above mixed reaction solution and obtain the above 3 compounds, of which 3,4,5-Trichlorobenzotrifluoride is used in next ammoniation reaction.

Example 3-Example 8

The unit and operation procedures are same to that of example 2, except change of some reaction conditions and feed ratio, with results shown in Table 1.

TABLE 1

Test results under different process conditions

|  |  |  |  | Reaction temperature (° C.), |  | Compositions of chlorides (%), GC |  |
|---|---|---|---|---|---|---|---|
| Examplee | Chlorobenzo-trifluorie | Powdered iron (g) | Anhydrous ferric chloride (g) | quantity of chlorine (g) | Purity of 3,4-Dichlorobenzo-trifluoride | Purity of 3,4,5-Trichloro-benzo-trifluoride | Purity of 2,4,5-trichloro-trifluoromethyl benzene |
| 3 | 1000 | 5 | 10 | 110, 825 | 69.47 | 20.29 | 9.66 |
| 4 | 800 | 6 | 12 | 110, 927 | 71.22 | 18.64 | 8.87 |
| 5 | 1000 | 5 | 10 | 115, 908 | 70.76 | 19.20 | 9.14 |
| 6 | 1000 | 6 | 10 | 115, 836 | 69.76 | 21.20 | 8.67 |
| 7 | 1000 | 6 | 10 | 60, 394 | 32.58 | 5.24 | 1.95 |
| 8 | 1000 | 6 | 10 | 120, 2368 | 30.48 | 16.21 | 7.29 |

Example 9

Preparation of the 2,6-dichloro-4-trifluoromethyl-aniline

Into a 1000 ml high-pressure reaction vessel add 200 g 3,4,5-Trichlorobenzotrifluoride and 145 g water, enclose the reaction vessel, fill liquid ammonia 380 g, close the valve, start agitation, slowly increase temperature to 160° C. and pressure to 10.0 MPa, make timed temperature-retention under controlled temperature 165° C. and controlled pressure 11.5 MPa for 8 h, then release the pressure and discharge ammonia.

After washing, rectify crude reaction products, recover the unreacted raw materials the 3,4,5-Trichlorobenzotrifluoride 20.4 g, and obtain the 2,6-dichloro-4-trifluoromethyl-aniline 120 g (content 99.24%) at yield 72.48%.

Example 10-Example 19

The unit and operation procedures are same to that of example 7, with results shown in Table 2.

Example 20

Into a 1000 L high-pressure reaction vessel add 200 kg the 3,4,5-Trichlorobenzotrifluoride, 130 kg water and 360 kg liquid ammonia, enclose the reaction vessel, start agitation, slowly increase temperature to 170° C., set the initial pressure at 0.2 MPa, make timed temperature-retention under controlled temperature 170±5° C. and controlled pressure 11.0 MPa~12.0 MPa for 9 h, then cool the product to 100° C., release pressure (pressure in stage 1 ammonia absorbing tank controlled at 0 MPa~1.8 MPa) and discharge ammonia, and make cooling with chilled saline. If during ammonia discharge the pressure in stage 1 ammonia absorbing tank is above 1.8 MP, absorb ammonia through stage 2 absorbing tank with pressure controlled at 0 MPa~1.2 MPa. After pressure relief, make discharge, wash the discharged substances and the reactants, and dewater the washed substances under high vacuum for 4 h (vacuum controlled at 0.09 MPa~0.095 MPa and temperature at 65° C.~85° C.).

After dewatering, make rectification and recover unreacted raw materials the 3,4,5-Trichlorobenzotrifluoride 20 kg for further utilization in ammoniation reaction. In addition,

TABLE 2

Test results under different process conditions

| Example | Trichlorobenzotrifluoride | Liquid ammonia (g) + H$_2$O (g) | Reaction temperature (° C.) | Reaction pressure (Mpa) | unreacted 3,4,5-Tri-chlorobenzo-trifluoride (g) | Purity of 2,6-dichloro-4-trifluoromethyl-aniline (%) | Yield of 2,6-dichlor0-4-trifluoromethyl-aniline (%) |
|---|---|---|---|---|---|---|---|
| 10 | 200 | 340 + 150 | 165 | 11.5 | 20.2 | 99.43 | 70.60 |
| 11 | 200 | 340 + 130 | 165 | 11.5 | 20.6 | 99.64 | 75.69 |
| 12 | 200 | 340 + 100 | 165 | 11.5 | 20.3 | 99.20 | 70.54 |
| 13 | 195 | 340 + 150 | 165 | 11.5 | 19.8 | 99.19 | 73.44 |
| 14 | 190 | 340 + 150 | 165 | 11.5 | 19.4 | 99.32 | 71.39 |
| 15 | 200 | 340 + 150 | 150 | 13.5 | 22.4 | 99.14 | 69.72 |
| 16 | 200 | 340 + 150 | 178 | 8.0 | 28.6 | 99.28 | 64.68 |
| 17 | 200 | 340 + 150 | 155 | 13.0 | 21.8 | 99.12 | 69.88 |
| 18 | 200 | 340 + 150 | 175 | 11.0 | 16.4 | 99.32 | 69.24 |
| 19 | 200 | 340 + 150 | 165 | 12.0 | 17.8 | 99.41 | 68.42 | obtain target product the 2,6-dichloro-4-trifluoromethyl-aniline 116.2 kg at content above 99.0% and yield 70.02%.

Example 21

The analyzed concentration of ammonia water in stage 1 absorbing tank is 40.2%. Take the said ammonia water 217.4 kg to ammonia-compounding tank and add fresh liquid ammonia 273.2 kg to this tank.

To 1000 L high-pressure reaction vessel add 3,4,5-Trichlorobenzotrifluoride 200 kg, add high-concentration ammonia water prepared in ammonia-compounding tank to the said high-pressure vessel, enclose the reaction vessel and conduct other operations as example 13.

After rectification, recover unreacted raw materials the 3,4,5-Trichlorobenzotrifluoride 18 kg and obtain target product the 2,6-dichloro-4-trifluoromethyl-aniline 118.5 kg at content above 99.0% and yield 70.63%.

The documents cited herein are used as reference in this application and they shall be deemed as be separately referenced. After reading this invention, any technician in this field may change or modify this invention, which is also within the claimed range hereof.

The invention claimed is:

1. A preparation method of 2,6-dichloro-4-trifluoromethylaniline (I), including the following steps:
    a) p-Chlorobenzotrifluoride (III) and chlorine are reacted at mole ratio 1:1~6 with elemental metal and metal halide as catalyst under reaction temperature of 50° C.~150° C., after completion of reaction separate the reaction product to obtain 3,4,5-Trichlorobenzotrifluoride (II);
    b, Put the 3,4,5-Trichlorobenzotrifluoride (II) obtained in the step a) and liquid ammonia together at mole ratio 1:6~40, add proper amount of water to control concentration of the liquid ammonia between 60 wt~80 wt %, make them react under reaction temperature of 150° C.~178° C. and reaction pressure of 1.0 MPa~13.5 MPa for 1~30 h, then separate the reaction product to obtain 2,6-dichloro-4-trifluoromethylaniline (I);

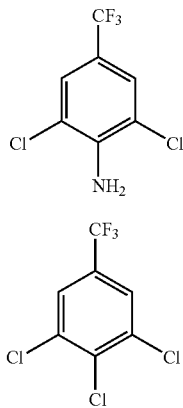

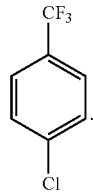

2. The preparation method according to claim 1, wherein said step a) the reaction temperature is 60° C.~120° C., a mole ratio of the elemental metal over the metal halide is 1:0.06~20, the dosage of the elemental metal is 0.2%~20% weight of the p-Chlorobenzotrifluoride (III) and the dosage of the metal halide is 0.2%~20% weight of the p-Chlorobenzotrifluoride (III).

3. The preparation method according to claim 1, wherein said step a) the reaction temperature is 100° C.~120° C., the dosage of the elemental metal is 0.2%~5% weight of p-Chlorobenzotrifluoride (III) and the dosage of the metal halide is 1%~10% weight of the p-Chlorobenzotrifluoride (III).

4. The preparation method according to claim 1, wherein said step a) the elemental metal is iron or aluminum and the metal halide is ferric chloride or aluminum chloride.

5. The preparation method according to claim 1, wherein said catalyst is a mixture of powdered metal iron and anhydrous ferric chloride.

6. The preparation method according to claim 1, wherein said step b) the mole ratio of the 3,4,5-Trichlorobenzotrifluoride (II) over the liquid ammonia is 1:10~27, the concentration of the liquid ammonia is 60 wt %~80 wt %, the reaction temperature is 155° C.~178° C., the reaction pressure is 8.0 MPa~13.0 MPa and reaction time 6~16 h.

7. The preparation method according to claim 1, wherein said step b) the mole ratio of the 3,4,5-Trichlorobenzotrifluoride (II) over the liquid ammonia is 1:20~26, the mass concentration of the liquid ammonia is 65 wt %~78 wt %, the reaction temperature is 165° C.~175° C., the reaction pressure is 11.0 MPa~12.0 MPa and reaction time is 8~12 h.

8. The preparation method according to claim 1, wherein in the step b) further includes recovery of ammonia from the surplus liquid ammonia.

9. The preparation method according to claim 8, wherein said recovery of ammonia is completed through absorbing by 2-stage pressurized absorbing tanks, the pressure of the first stage absorbing tank is controlled at 0 MPa~2.5 MPa.

10. The preparation method according to claim 8, wherein said recovery of ammonia is completed through absorbing by 2-stage pressurized absorbing tanks, the pressure of the first stage absorbing tank is controlled at 0 MPa~2.0 MPa.

* * * * *